United States Patent [19]

Kelman

[11] Patent Number: 4,538,611
[45] Date of Patent: Sep. 3, 1985

[54] SURGICAL INSTRUMENT AND METHOD OF CUTTING A LENS OF AN EYE

[76] Inventor: Charles D. Kelman, North Shore Towers, 269 Grand Central Pkwy., Bldg. 3, Floral Park, N.Y. 11005

[21] Appl. No.: 503,637

[22] Filed: Jun. 13, 1983

[51] Int. Cl.³ .............................................. A61B 17/32
[52] U.S. Cl. ...................................... 128/305; 604/22
[58] Field of Search ................... 128/305, 320; 604/22

[56]  References Cited

U.S. PATENT DOCUMENTS

| | | | |
|---|---|---|---|
| 668,647 | 2/1901 | Jaenicke | 128/320 |
| 798,839 | 9/1905 | Stowe | 128/320 |
| 1,225,771 | 5/1917 | Clare | 128/320 |
| 1,310,982 | 7/1919 | Davis | 128/320 |
| 2,294,852 | 9/1942 | Smith . | |
| 2,856,933 | 10/1958 | Hildenbrand et al. . | |
| 3,181,533 | 5/1965 | Heath | 128/320 |
| 4,202,338 | 5/1980 | Bitrolf | 128/320 |
| 4,345,599 | 8/1982 | McCarrell | 128/320 |
| 4,440,169 | 4/1984 | Schulman | 128/305 |

*Primary Examiner*—C. Fred Rosenbaum
*Assistant Examiner*—Gene B. Kartchner
*Attorney, Agent, or Firm*—Henry Sternberg

[57] ABSTRACT

A surgical instrument for cutting a lens of a human eye inside the eye for removal through a small incision in the cornea. The instrument has a flange at its front end and a snare loop extending through the flange for ensaring the lens and cutting the same while the lens is supported by the flange.

11 Claims, 4 Drawing Figures

SURGICAL INSTRUMENT AND METHOD OF CUTTING A LENS OF AN EYE

This invention relates to a surgical instrument for cutting a lens of an eye, and, more particularly, to a surgical instrument for cutting a cataracted lens of a human eye inside the eye. The invention also relates to a method of cutting a lens of an eye, and, more particularly, to a method of cutting a cataracted lens of a human eye inside the eye.

U.S. Pat. No. 2,856,933 describes a surgical snare for cutting animal tissue for subsequent removal. This patent, however, does not suggest an instrument which is capable of cutting a cataracted lens of an eye and does not suggest that it is desirable to cut a cataracted lens of an eye inside the eye.

Heretofore, for those surgeons who, either because of their own preference or because in their opinion a particular patient was not a good candidate for it, preferred not to use the Phaco-Emulsifier method for the removal of a cataracted lens from an eye, it has been necessary for the surgeon to cut an incision in the cornea of the eye sufficiently large that the cataracted lens could be removed. The cataracted lens may have a diameter of, for example, 10 mm and the incision in the cornea was, therefore, slightly greater than 10 mm. However, it is desirable that the incision in the cornea be made as small as possible to minimize the possibility of injury to the eye.

I propose a surgical instrument for cutting the cataracted lens of the eye inside the eye approximately in half and removing the halves of the cataracted lens separately through a small incision of, for example, 6 mm.

It is an object of the invention, therefore, to provide a new and improved surgical instrument for cutting a lens of an eye which avoids one or more of the disadvantages and limitations of prior surgical instruments.

It is another object of the invention to provide a new and improved surgical instrument for cutting a cataracted lens of a human eye inside the eye.

It is another object of the invention to provide a new and improved method of cutting a lens of an eye which avoids one or more of the disadvantages and limitations of prior methods.

It is another object of the invention to provide a new and improved method of cutting a cataracted lens of a human eye inside the eye approximately in half for subsequent removal.

In accordance with the invention, a surgical instrument for cutting the lens of an eye comprises a first body member having a front end and having a second member movably supported therein for movement between a forward position and a retracted position. The first body member has at the front end a flange extending transversely thereto. The instrument also includes a snare loop extending outwardly through the front end of the first body member and the flange and having one end attached to one of the first and second body members and the other end attached to the second member, whereby the loop can be enabled to snare a lens of an eye and to cut the same while the lens of the eye is supported by the flange.

Also in accordance with the invention, a method of cutting an interior portion of an eye comprises inserting into the eye the front end of the first body member of a surgical instrument having a second member movably supported therein for movement manually between a forward position and a retracted position. The first body member has at the front end thereof a flange extending transversely thereto and the surgical instrument has a snare loop extending outwardly through the front end of the first body member and the flange and has one end attached to one of the first and second body members and the other end attached to the second member. The method includes the step of surrounding the interior portion of the eye with the snare loop and the flange. The method also includes the step of moving the second member in the first body member to diminish the size of the snare loop, thereby pressing the lens of the eye against the flange and cutting the lens of the eye with the snare loop.

For a better understanding of the present invention, together with other objects thereof, reference is made to the following description, taken in connection with the accompanying drawings, and its scope will be pointed out in the appended claims.

Referring now to the drawings.

Figure 1:
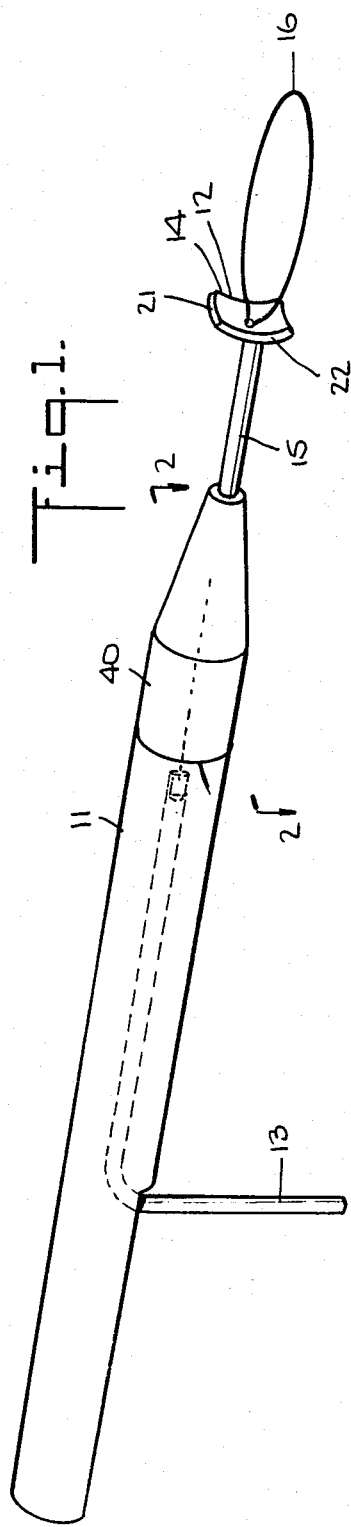
FIG. 1 is a perspective view of a surgical instrument constructed in accordance with the invention.
Figure 2:
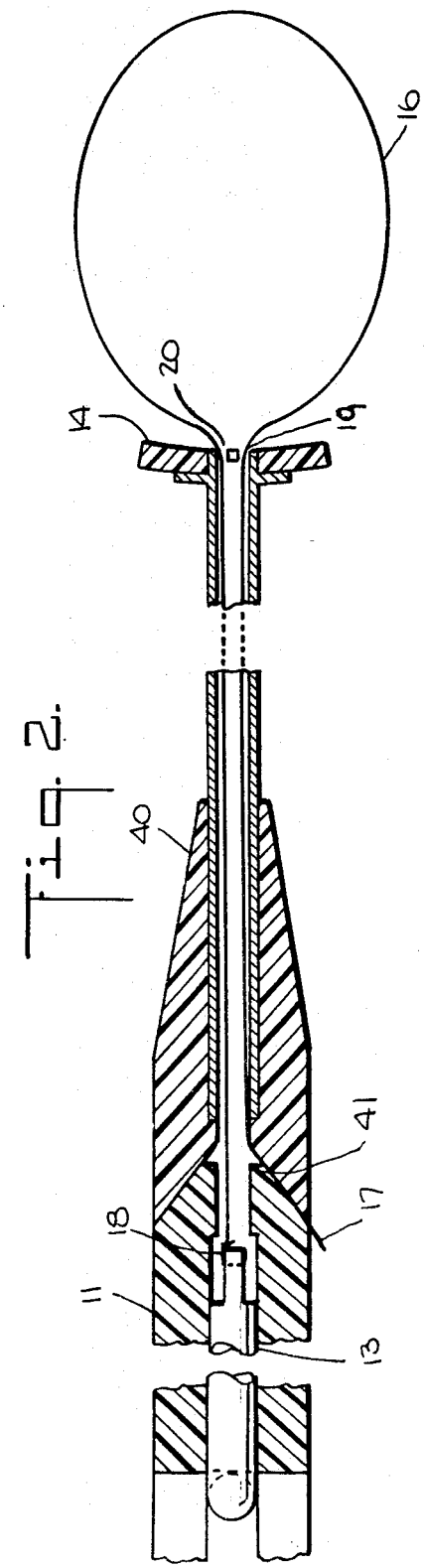
FIG. 2 is a fragmentary sectional view, to an enlarged scale, of the FIG. 1 instrument, taken along line 2—2 of FIG. 1.

Referring now more particularly to FIGS. 1 and 2 of the drawings, a surgical instrument for cutting a lens of an eye comprises a first body member 11 having a front end 12 and having a second member 13 movably supported in the first body member 11 for movement between a forward position as represented in FIGS. 1 and 2 and a retracted position. The first body member 11, which may be of metal or plastic material has at its front end 12 a flange 14, which may be of inert plastic material, extending transversely to the first body member 11. The first body member includes a sleeve 15 which may be of metal or inert plastic material, extending to the flange 14. The first body member 11 also includes a tip portion 40 which may be force fitted over the stem 41 of the body portion 11.

The surgical instrument includes a snare loop 16 extending outwardly through the front end 12 of the first body member 11 and the flange 14 and having one end 17 attached to one of the first and second body members 11, 13, and preferably attached to the first body member 11 and the other end 18 attached to the second member 13, whereby the loop 16 can be enabled to ensnare a lens of an eye and to cut the same while the lens of the eye is supported by the flange 14. The loop 16 has a portion extending outwardly through the sleeve 15 and through apertures 19, 20 of the flange 14.

The loop 16 preferably is of nylon or metal wire. The width 21 of the flange 14 may, for example, be 1 mm and the length 22 of the flange 14 may, for example, be 1.5 mm. The flange 14 preferably is curved along the dimensions 21 and 22 for supporting the lens while the loop 16 is enabled to cut the lens.

Figure 3:
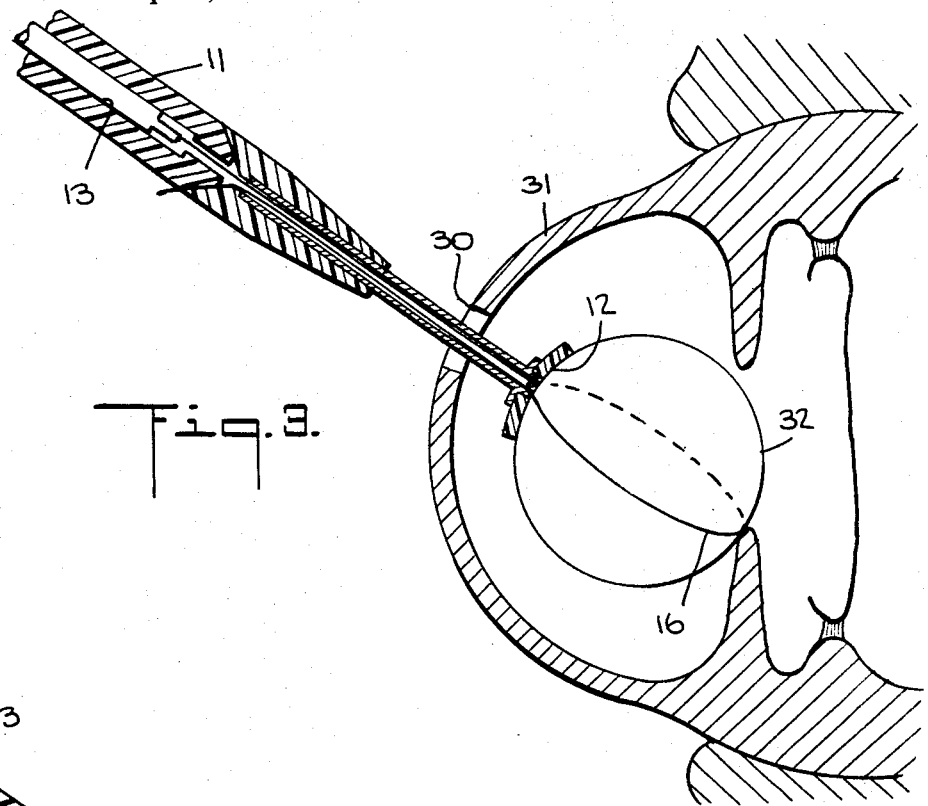
FIG. 3 is a fragmentary sectional view of the FIG. 1 instrument inserted into a human eye also shown in section and having snared the lens.
Figure 4:
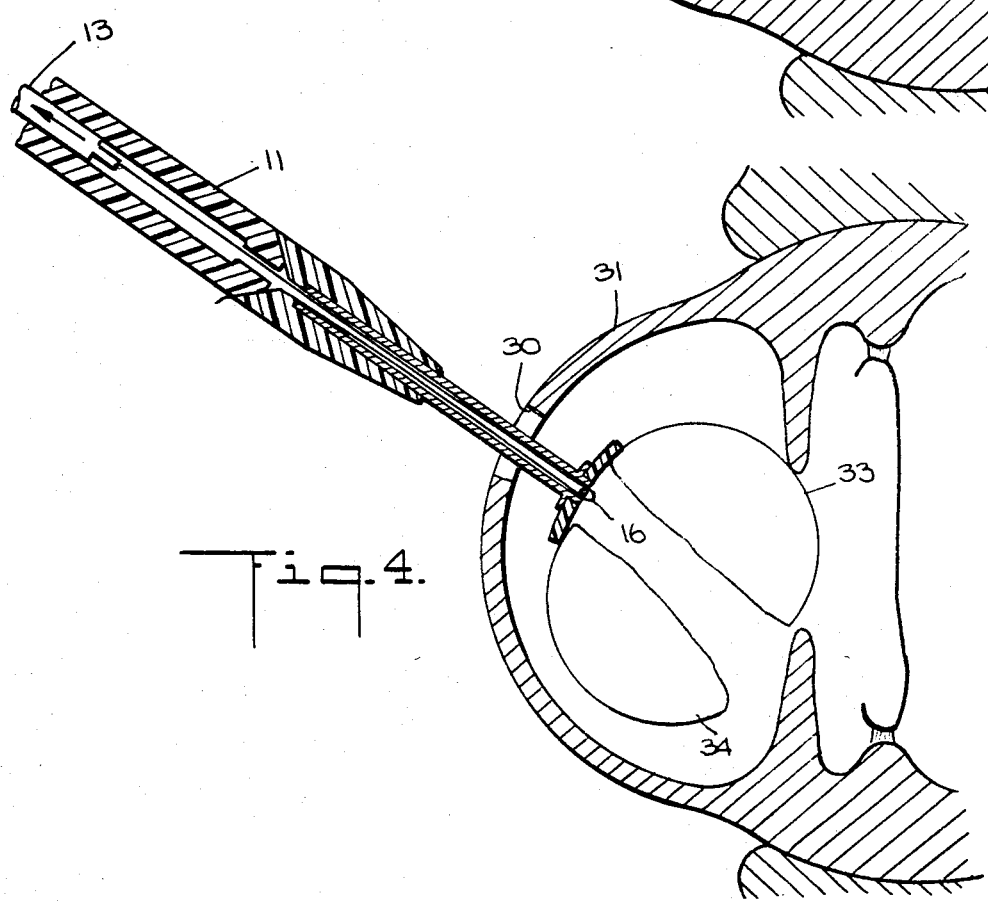
FIG. 4 is a fragmentary sectional view of the FIG. 1 instrument inserted into the eye also shown in section and having cut the lens.

Referring now more particularly to FIGS. 3 and 4 of the drawings, a relatively small incision 30 is made in the cornea 31, for example, only about 6 mm in length. The cataracted lens is moved into the anterior chamber by the surgeon, and the anterior chamber is deepened by injecting a viscoelastic inert substance such as Healon (a registered trademark), therein. The method of cutting the lens of the eye in accordance with the invention comprises inserting into the eye the front end 12 of the first body member 11 and surrounding the lens 32 with the snare loop 16 and the flange 12 as represented in FIG. 3. Preferably, the snare loop is positioned approximately around an equator of the lens to enable the snare loop to cut the lens approximately in half inside the eye.

The method also comprises moving the second member 13 in the first body member to diminish the size of the snare loop, thereby pressing the lens 32 of the eye against the flange 14 as represented in FIG. 3 and cutting the lens 32 of the eye with the snare loop as represented in FIG. 4. The two halves 33, 34 of the lens may then readily be removed by the surgeon through the small incision 30.

The lens is sufficiently soft that the flange 14 must be utilized in cooperation with the snare loop 16 to enable the snare loop 16 to cut the lens as desired.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit nad scope of the invention.

What is claimed is:

1. A surgical instrument for cutting a lens of an eye comprising:
   a first body member having a front end and having a second member movably supported in said first body member for movement between a forward position and a retracted position,
   said first body member having at said front end a flange extending transversely thereto and said flange having a concave front face, and
   a snare loop extending outwardly through said front end of said first body member and said flange and having one end attached to one of said first and second body members and the other end attached to said second member, whereby said loop can be enabled to ensnare a lens of an eye and to cut the same while the lens of the eye is supported by said concave front face of said flange.

2. A surgical instrument in accordance with claim 1 in which said first body member includes a sleeve extending to said flange and in which said loop has a portion extending outwardly through said sleeve and said flange.

3. An instrument in accordance with claim 1 in which said loop is of nylon.

4. An instrument in accordance with claim 1 for cutting the lens of an eye in which said flange supports the lens while said loop is enabled to cut the lens.

5. An instrument in accordance with claim 4 in which said front face of said flange is concavely curved so as to approximate the contour of the edge of the lens supported thereon.

6. An instrument in accordance with claim 4 in which said front face of said flange is concavely curved in several directions.

7. An instrument in accordance with claim 4 in which said flange has a length substantially greater than its width.

8. An instrument in accordance with claim 4 wherein said flange has dimensions sufficiently small as to permit it to be inserted into the interior of the eye through an incision no larger than is required for removal therethrough of a cut portion of the lens.

9. An instrument in accordance with claim 7 wherein said snare loop is generally in a plane transverse to the length direction of elongation of said flange.

10. A method of cutting a lens of an eye comprising:
    moving the lens of the eye into the anterior chamber of the eye;
    inserting into the eye the front end of a first body member of a surgical instrument having a second member movably supported in the first body member for movement manually between a foward position and a retracted position, the first body member having at the front end thereof a flange extending transversely thereto, the surgical instrument having a snare loop extending outwardly through the front end of the first body member and the flange and having one end attached to one of the first and second body members and the other end attached to the second member;
    surrounding the lens of the eye with the snare loop and the flange; and
    moving the second member in the first body member to diminish the size of the snare loop, thereby pressing the lens of the eye against the flange and cutting the lens of the eye with the snare loop.

11. A method in accordance with claim 10 in which the step of surrounding the lens of the eye with the snare loop and the flange comprises positioning the snare loop approximately around an equator of the lens to enable the snare loop to cut the lens approximately in half inside the eye.

* * * * *